United States Patent
Abkowitz et al.

(10) Patent No.: US 8,119,773 B2
(45) Date of Patent: Feb. 21, 2012

(54) COMPOSITIONS AND METHODS FOR FACILITATING HEME-IRON EXPORT FROM CELLS

(75) Inventors: Janis L. Abkowitz, Mercer Island, WA (US); Raymond T. Doty, Seattle, WA (US); Zhantao Yang, Kenmore, WA (US)

(73) Assignee: University of Washington, Seattle, WA (US)

( * ) Notice: Subject to any disclaimer, the term of this patent is extended or adjusted under 35 U.S.C. 154(b) by 242 days.

(21) Appl. No.: 12/329,206

(22) Filed: Dec. 5, 2008

(65) Prior Publication Data

US 2009/0149383 A1     Jun. 11, 2009

Related U.S. Application Data

(60) Provisional application No. 61/012,196, filed on Dec. 7, 2007.

(51) Int. Cl.
    *C07K 14/00*     (2006.01)
(52) U.S. Cl. ....................................... 530/385
(58) Field of Classification Search .................. 530/385
    See application file for complete search history.

(56) References Cited

OTHER PUBLICATIONS

Yang et al. Nov. 16, 2007; Evidence that heme export via the feline leukemia virus, subgroup C receptor (FLVCR) is carrier dependent and its physiological implications. Blood (ASH Annual Meeting Abstracts) 110: Abstract 2659.*

Takahashi et al. 1985. Complete amino acid sequence of human hemopexin, the heme binding protein of serum. PNAS 82: 73-77.*

Quigley, JG et al., "Identification of a human heme exporter that is essential for erythropoiesis" Cell 118:757-766, 2004.

Paoli, M et al., "Crystal structure of hemopexin reveals a novel high-affinity heme site formed between two . . . domains", Nature Structural Biology 6, 926-931,1999.

Lipovich, L et al., "Genomic structure and evolutionary context of the human feline leukemia virus subgroup C receptor (hFLVCR) gene: evidence . . . locus" Gene 286:203-213, 2002.

Vardy, E et al., "Structural conservation in the major facilitator superfamily as revealed by comparative modeling" Protein Science, V13, N7, pp. 1832-1840, 2004.

* cited by examiner

*Primary Examiner* — Karen Carlson
(74) *Attorney, Agent, or Firm* — Karen S. Canady; canady + lortz LLP

(57) ABSTRACT

The invention provides a high affinity heme-binding agent, which can be provided in the form of a pharmaceutical composition that includes, optionally, a pharmaceutically acceptable carrier. The heme-binding agent can be used in a method of facilitating heme-iron export from a cell. The method comprises contacting a cell with a high affinity heme-binding agent. Also provided is a method of treating a disorder associated with excess iron in cells in a subject. The method comprises administering to the subject an effective amount of the composition of the invention. The subject is typically a mammal, most typically a human or veterinary subject.

20 Claims, 8 Drawing Sheets

Control      Mouse lacking FLVCR in BM

COMPOSITIONS AND METHODS FOR FACILITATING HEME-IRON EXPORT FROM CELLS

This application claims benefit of U.S. provisional patent application No. 61/012,196, filed Dec. 7, 2007, the entire contents of which are incorporated by reference into this application.

STATEMENT REGARDING FEDERALLY SPONSORED RESEARCH

This invention was made with government support under grant number HL31823 awarded by the National Institutes of Health (NIH). The government has certain rights in the invention.

TECHNICAL FIELD OF THE INVENTION

The present invention relates generally to facilitating heme-iron export from cells. More specifically, the invention relates to a high affinity heme-binding agent, and its use in compositions and methods of facilitating heme-iron export from cells and for treating disorders associated with excess iron in cells.

BACKGROUND OF THE INVENTION

Free heme is toxic, but also critical as the prosthetic component of hemoproteins such as cytochromes, DNA synthetic enzymes, hemoglobin, and myoglobin, and as a transcriptional and translation regulator of gene expression. Differentiating red blood cells must export heme through a heme export protein called feline leukemia virus receptor (FLVCR; Cell 118:757, 2004) to survive. In addition, macrophages export heme via FLVCR to recycle the heme-iron from senescent red blood cells (see Example 1 hereinbelow). Failure to control free heme and/or maintain an iron balance in cells results in various disorders. The liver likely exports heme via FLVCR to bile then feces, providing a route for iron to exit the body. There remains a need for effective methods of facilitating heme export from cells and to mitigate systemic iron overload.

SUMMARY OF THE INVENTION

The invention provides a high affinity heme-binding agent, which can be provided in the form of a pharmaceutical composition that includes, optionally, a pharmaceutically acceptable carrier. The heme-binding agent can be used in a method of facilitating heme-iron export from a cell. The method comprises contacting a cell with a high affinity heme-binding agent. Also provided is a method of treating a disorder associated with excess iron in cells in a subject. The method comprises administering to the subject an effective amount of the composition of the invention. The subject is typically a mammal, most typically a human or veterinary subject.

In one embodiment, the disorder associated with excess iron in cells is the anemia associated with inflammation. Examples of anemia associated with inflammation (or inflammatory block) include rheumatoid arthritis and anemia that is secondary to infection. In these circumstances, iron accumulates in macrophage cells and can not be recycled to developing red cells. Usually, macrophages digest senescent red cells and then recycle the iron that is contained within the hemoglobin molecules by exporting inorganic iron (via ferroportin). The inventors have shown that, in addition, iron can be exported as heme via FLVCR. The exit of inorganic iron is blocked when there is inflammation. Anemia occurs because developing red cells have insufficient iron. Macrophage recycling could be facilitated by maximizing the exit of heme-iron using the method of this invention.

In another embodiment, method is directed at certain other types of anemia, such as that which occurs with myelodysplasia, the macrocytic anemias, and anemias related to ineffective erythropoiesis. These latter anemias result from an imbalance of heme relative to globin. It appears that free heme is toxic to the developing red cell. By facilitating the export of excess heme, the method of the invention can help reduce this imbalance and thus improve red cell production.

In another embodiment, the disorder is related to systemic iron overload, such as occurs with hemochromatosis or related disorders. Related disorders include iron-overload from transfusion or chronic hemolysis In this type of disorder, the method of the invention can be used to facilitate export of excess heme-iron into the stool via bile and thus out of the body. The invention can also be used in disorders where the excess of iron in cells leads to cell-specific toxicities. These include cellular iron stress due to iron overload in cells and oxidative stress. Because the heme-transporter FLVCR is highly expressed in tissues such as brain and kidney, the method of the invention can be used to reduce tissue damage in these areas that is caused by such stress.

The administering can be intravenous or subcutaneous, or in some embodiments, oral. The route of administration is selected based primarily on the nature of the heme-binding agent in use. Those skilled in the art will appreciate that proteins, and polynucleotides encoding proteins, are likely best delivered intravenously or subcutaneously, while smaller molecules and some bacterial hemophores are likely suitable for oral administration.

Typically the heme-binding agent is hemopexin (a naturally and physiologically important occurring heme binding protein), a high affinity synthetic heme binder or a bacterial hemophore. Bacterial hemophores are attractive candidates for therapeutic applications due to their potential lack of toxicity. Representative heme-binding agents include hemopexin, heme-binding protein 23 (HBP23; also known as peroxiredoxin I or Prx I); adrenal inner zone antigen (IZA1); rhodnius heme-binding protein (RHBP); NADPH-dependent methemoglobin reductase; histidine-rich protein 2 (HRP-2); damage resistance protein 1 (Dap1p); and HupA, a heme receptor on the cytoplasmic membrane of $E.\ coli$. Some additional bacterial heme-binding proteins include: the periplasmic lipoprotein HpbA of $H.\ Influenzae$; the heme shuttle protein ShuT from $S.\ dysenteriae$; the heme transport proteins PhuS from $P.\ aeruginosa$ and HemS from $Y.\ enterocolitica$. Any agent that binds heme, particularly with high affinity, can be used in the methods of the invention. Typically, the heme-binding agent has a Kd of up to about 1 nM, or in some embodiments, up to about 1 μM.

(7A) FLVCR mRNA expression by quantitative RT-PCR. Data represent the average of three separate analyses normalized to the percent of wild-type liver mRNA levels. Flvcr$^{+/+}$ mice (hatched bars) n=8, Flvcr$^{+/-}$ mice (solid bars) n=8 for all tissues except bone marrow where n=5 for both groups. (7B) FLVCR protein expression in bone marrow (BM), liver, and spleen by densitometry of the 60 kB FLVCR band on western blots. Data represent the average intensity from three western blots normalized to control mice liver samples. Flvcr$^{+/+}$ mice n=8, Flvcr$^{+/-}$ mice n=9 for all tissues except bone marrow where n=6 for both groups.

Figure 8:
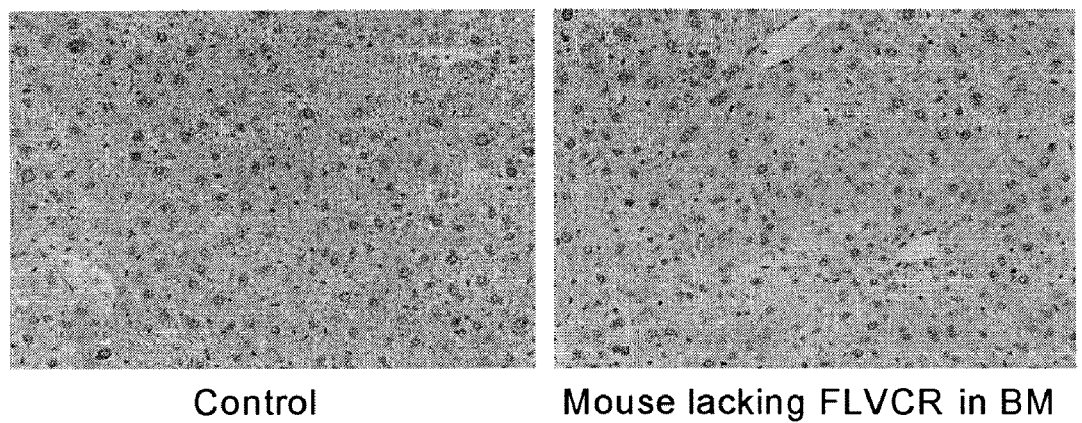

FIG. 8. Liver of a mouse lacking FLVCR only in the bone marrow. Representative Prussian blue (for iron) stained liver sections from a control mouse and a mouse transplanted with Flvcr$^{flox/flox}$; Mx-cre$^+$ marrow and then treated to delete Flvcr in hematopoietic cells. Liver sections obtained 5.5 weeks post poly(I)-poly(C) treatment (deletion).

Figure 9A:
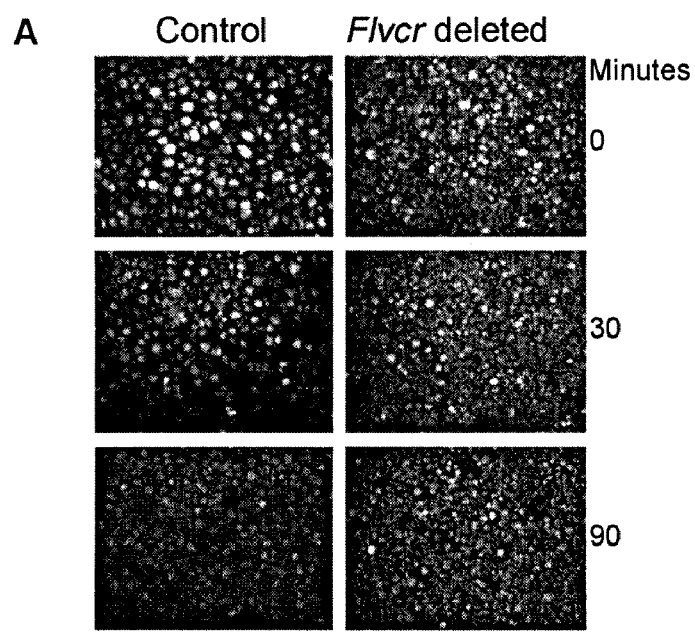
Figure 9B:
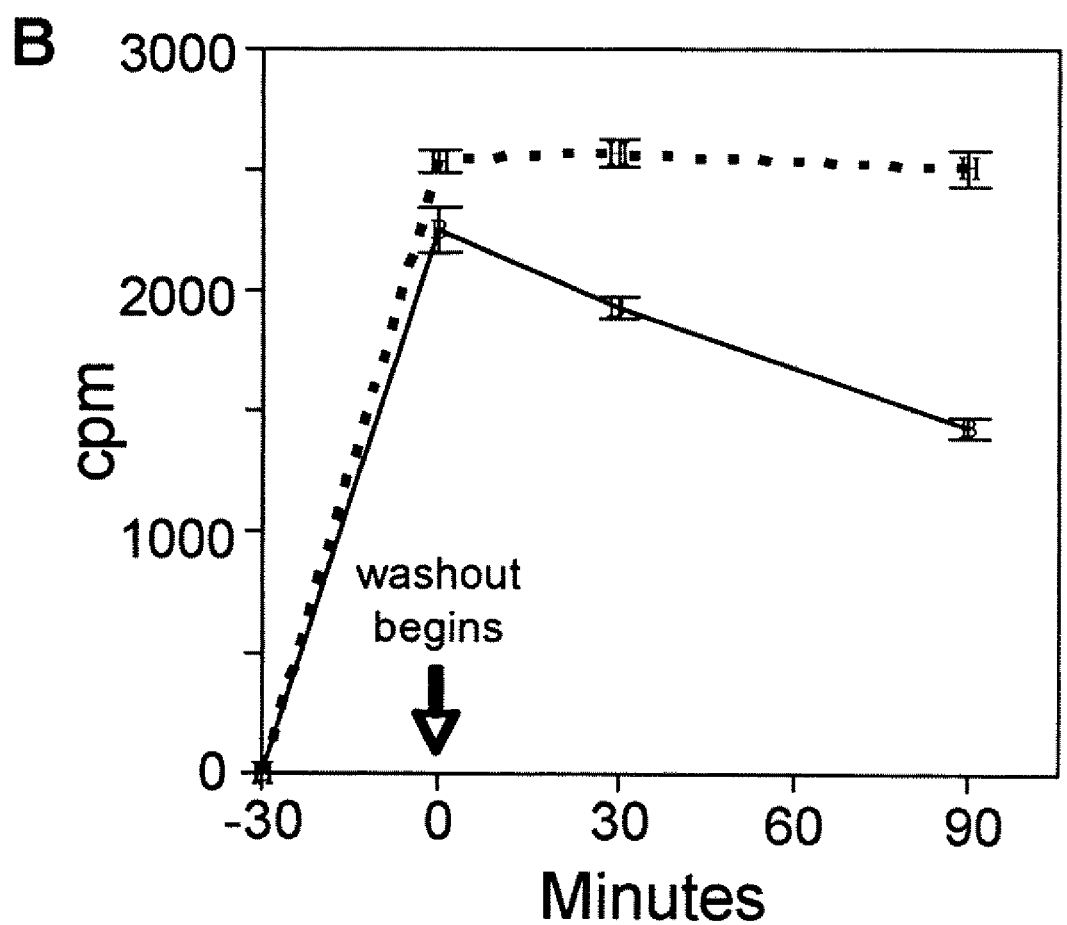

FIGS. 9A-9B. Flvcr-deleted macrophages have impaired export of the heme analog ZnMP and $^{55}$Fe-heme. (9A) Macrophages from the bone marrow of adult control and Flvcr-deleted littermates (Flvcr$^{flox/flox}$; Mx-cre$^+$) were incubated with ZnMP (5 µM) for 30 minutes at 37° C., then washed and incubated for 30, and 90 minutes in buffer alone at 37° C. (9B) Fe$^{55}$-heme export studies performed similarly to A. control mouse (solid) and Flvcr-deleted mouse (dashed). Radioactivity is expressed as a mean of triplicate samples (±SD).

DETAILED DESCRIPTION OF THE INVENTION

The invention is based on the discovery that heme export depends on having a strong heme-binding protein on the outside of the cell. Heme export efficiency via feline leukemia virus receptor (FLVCR) depends on the presence of a protein outside the cell that can avidly and specifically bind heme, such as hemopexin. This export efficacy is kd and carrier concentration dependent.

Definitions

All scientific and technical terms used in this application have meanings commonly used in the art unless otherwise specified. As used in this application, the following words or phrases have the meanings specified.

As used herein, "polypeptide" includes proteins, fragments of proteins, and peptides, whether isolated from natural sources, produced by recombinant techniques or chemically synthesized. Polypeptides of the invention typically comprise at least about 6 amino acids, and can be at least about 15 amino acids. Those skilled in the art also recognize that additional adjacent sequence from the original (native) protein can be included, and is often desired, in an effective polypeptide suitable for use in a composition of the invention. This adjacent sequence can be from 1, 2, 3, 4, 5, 6, 7, 8, 9 or 10 amino acids in length to as much as 15, 20, 25, 30, 35, 40, 45, 50, 75 or 100 amino acids in length or more.

As used herein, particularly in the context of polypeptides of the invention, "consisting essentially of" means the polypeptide consists of the recited amino acid sequence and, optionally, adjacent amino acid sequence. The adjacent sequence typically consists of additional, adjacent amino acid sequence found in the full length native protein, but variations from the native protein can be tolerated in this adjacent sequence while still providing a biologically active polypeptide. Those skilled in the art recognize that certain variations are less likely than others to disrupt the structure, conformation and activity of the polypeptide.

As used herein, "substitutional variant" refers to a molecule having one or more amino acid substitutions or deletions in the indicated amino acid sequence, yet retaining functional activity. The amino acid sequence of a substitutional variant is typically at least 90% identical to the native amino acid sequence. Typically, the substitution is a conservative substitution.

As used herein, "vector" means a construct, which is capable of delivering, and preferably expressing, one or more gene(s) or sequence(s) of interest in a host cell. Examples of vectors include, but are not limited to, viral vectors, naked DNA or RNA expression vectors, plasmid, cosmid or phage vectors; DNA or RNA expression vectors associated with cationic condensing agents, DNA or RNA expression vectors encapsulated in liposomes, and certain eukaryotic cells, such as producer cells.

As used herein, "expression control sequence" means a nucleic acid sequence that directs transcription of a nucleic acid. An expression control sequence can be a promoter, such as a constitutive or an inducible promoter, or an enhancer. The expression control sequence is operably linked to the nucleic acid sequence to be transcribed.

As used herein, "operably connected" or "operably linked" and the like is meant a linkage of polynucleotide elements in a functional relationship. A nucleic acid is "operably linked" when it is placed into a functional relationship with another nucleic acid sequence. For instance, a promoter or enhancer is operably linked to a coding sequence if it affects the transcription of the coding sequence. Operably linked means that the nucleic acid sequences being linked are typically contiguous and, where necessary to join two protein coding regions, contiguous and in reading frame. "Operably linking" a promoter to a transcribable polynucleotide is meant placing the transcribable polynucleotide (e.g., protein encoding polynucleotide or other transcript) under the regulatory control of a promoter, which then controls the transcription and optionally translation of that polynucleotide.

The term "nucleic acid" or "polynucleotide" refers to a deoxyribonucleotide or ribonucleotide polymer in either single- or double-stranded form, and unless otherwise limited, encompasses known analogs of natural nucleotides that hybridize to nucleic acids in a manner similar to naturally occurring nucleotides.

As used herein, "pharmaceutically acceptable salt" refers to a salt that retains the desired biological activity of the parent compound and does not impart any undesired toxicological effects. Examples of such salts include, but are not limited to, (a) acid addition salts formed with inorganic acids, for example hydrochloric acid, hydrobromic acid, sulfuric acid, phosphoric acid, nitric acid and the like; and salts formed with organic acids such as, for example, acetic acid, oxalic acid, tartaric acid, succinic acid, maleic acid, fumaric acid, gluconic acid, citric acid, malic acid, ascorbic acid, benzoic acid, tannic acid, pamoic acid, alginic acid, polyglutamic acid, naphthalenesulfonic acids, naphthalenedisulfonic acids, polygalacturonic acid; (b) salts with polyvalent metal cations such as zinc, calcium, bismuth, barium, magnesium, aluminum, copper, cobalt, nickel, cadmium, and the like; or (c) salts formed with an organic cation formed from N,N'-dibenzylethylenediamine or ethylenediamine; or (d) combinations of (a) and (b) or (c), e.g., a zinc tannate salt; and the like. The preferred acid addition salts are the trifluoroacetate salt and the acetate salt.

As used herein, "pharmaceutically acceptable carrier" includes any material which, when combined with an active ingredient, allows the ingredient to retain biological activity and is non-reactive with the subject's immune system. Examples include, but are not limited to, any of the standard pharmaceutical carriers such as a phosphate buffered saline solution, water, emulsions such as oil/water emulsion, and various types of wetting agents. Preferred diluents for aerosol or parenteral administration are phosphate buffered saline or normal (0.9%) saline. Compositions comprising such carriers are formulated by well known conventional methods (see, for example, *Remington's Pharmaceutical Sciences,* 18th edition, A. Gennaro, ed., Mack Publishing Co., Easton, Pa., 1990).

As used herein, "a" or "an" means at least one, unless clearly indicated otherwise.

As used herein, to "prevent" or "protect against" a condition or disease means to hinder, reduce or delay the onset or progression of the condition or disease.

Compositions of the Invention

The invention provides a high affinity heme-binding agent, which can be provided in the form of a pharmaceutical composition that includes, optionally, a pharmaceutically acceptable carrier. The heme-binding agent can be used in the methods described below, relating to its ability to facilitate heme-iron export from cells. One example of high affinity in relation to heme-binding agents, is a Kd of less than about 1 nM. Typically, the heme-binding agent has a Kd of less than about 1 pM. The high affinity of the heme binding agent can be achieved through a high affinity binding site, or its functional equivalent can be achieved via multiple low affinity heme binding sites. A heme binding agent is high affinity if it can bind heme equivalently to or better than albumin in a competitive binding assay. One example of a competitive binding assay for heme is described in: *Biochim Biophys Acta* 444(2): 435-45, 1976.

Typically the heme-binding agent is hemopexin (a naturally and physiologically important occurring heme binding protein), a high affinity synthetic heme binder or a bacterial hemophore. Bacterial hemophores are attractive candidates for therapeutic applications due to their potential lack of toxicity. Representative heme-binding agents include hemopexin, heme-binding protein 23 (HBP23; also known as peroxiredoxin I or Prx I); adrenal inner zone antigen (IZA1); rhodnius heme-binding protein (RHBP); NADPH-dependent methemoglobin reductase; histidine-rich protein 2 (HRP-2); damage resistance protein 1 (Dap1p); and HupA, a heme receptor on the cytoplasmic membrane of *E. coli*. Some additional bacterial heme-binding proteins include: the periplasmic lipoprotein HpbA of *H. Influenzae*; the heme shuttle protein ShuT from *S. dysenteriae*; the heme transport proteins PhuS from *P. aeruginosa* and HemS from *Y. enterocolitica*. Any agent that binds heme, particularly with high affinity, can be used in the methods of the invention.

A high affinity heme binder can be synthesized using known techniques because the structural characteristics of common heme-binding sites are well-known: e.g., two histidines that are 43-52 amino acids apart with hydrophobic amino acids lining the heme binding pocket (See Nature Structural Biology 6:926, 1999). In one embodiment, the high affinity synthetic heme binder is a synthetic hemopexin or heme-binding portion thereof.

Hemopexin and evolutionarily related proteins have a 52 amino acid spacer between the histidines. In non-related heme-binding proteins, such as bacterial proteins, the linear spacer is not 52 amino acids. The model of human serum albumin binding heme has histidines located 45 amino acids apart. From these and other data, the actual linear spacing between the histidines is important to the extent that the histidines need to be spaced far enough apart that there is space for the porphyrin ring of heme to fit in the heme binding pocket. Common to the various heme-binders is that the heme pocket is lined with hydrophobic amino acids which can interact with the hydrophobic porphyrin ring of heme. Histidine is the most common amino acid used to coordinate heme binding in hemoproteins and appears to have the highest avidity, but a few other amino acids are used such as methionine, lysine, and tyrosine.

Hydrophobic amino acids are known in the art and include valine, isoleucine, leucine, methionine, phenylalanine, tyrosine, tryptophan, histidine, lysine, threonine, alanine, glycine, and cysteine.

Methods and Uses of the Invention

The invention provides a method of facilitating heme-iron export from a cell. The method comprises contacting a cell with a high affinity heme-binding agent Also provided is a method of treating a disorder associated with excess iron in cells in a subject. The method comprises administering to the subject an effective amount of the composition of the invention.

The subject is typically a mammal, most typically a human or veterinary subject. Examples of mammalian subjects include, but are not limited to, feline, canine, equine, porcine, bovine, ovine, primate, and rodent subjects.

In one embodiment, the disorder associated with excess iron in cells is the anemia associated with inflammation. Examples of anemia associated with inflammation (or inflammatory block) include rheumatoid arthritis and anemia that is secondary to infection. In these circumstances, iron accumulates in macrophage cells and can not be recycled to developing red cells. Usually, macrophages digest senescent red cells and then recycle the iron that is contained within the hemoglobin molecules by exporting inorganic iron (via ferroportin) and heme-iron (via FLVCR). The exit of inorganic iron is blocked when there is inflammation. Anemia occurs because developing red cells have insufficient iron. Macrophage recycling could be facilitated by maximizing the exit of heme-iron using the method of this invention.

In another embodiment, method is directed at certain other types of anemia, such as that which occurs with myelodysplasia, the macrocytic anemias, and anemias related to ineffective erythropoiesis. These latter anemias result from an imbalance of heme relative to globin. It appears that free heme is toxic to the developing red cell. By facilitating the export of excess heme, the method of the invention can help reduce this imbalance and thus improve red cell production.

In another embodiment, the disorder is related to systemic iron overload, such as occurs with hemochromatosis or related disorders. Related disorders include iron-overload from transfusion or chronic hemolysis. In this type of disorder, the method of the invention can be used to facilitate export of excess heme-iron into the stool via bile and thus out of the body. The invention can also be used in disorders where the excess of iron in cells leads to cell-specific toxicities. These include cellular iron stress due to iron overload in cells and oxidative stress. Because the heme-transporter FLVCR is highly expressed in tissues such as brain and kidney, the method of the invention can be used to reduce tissue damage in these areas that is caused by such stress.

Administration and Dosage

The compositions are administered in any suitable manner, often with pharmaceutically acceptable carriers. Suitable methods of administering compositions in the context of the present invention to a subject are available, and, although more than one route can be used to administer a particular composition, a particular route can often provide a more immediate and more effective reaction than another route.

The dose administered to a patient, in the context of the present invention, should be sufficient to effect a beneficial therapeutic response in the patient over time, or to inhibit disease progression. Thus, the composition is administered to a subject in an amount sufficient to elicit an effective response to the specific antigens and/or to alleviate, reduce, cure or at least partially arrest symptoms and/or complications from the disease. An amount adequate to accomplish this is defined as a "therapeutically effective dose."

The administering can be intravenous or subcutaneous, or in some embodiments, oral. The route of administration is selected based primarily on the nature of the heme-binding agent in use. Those skilled in the art will appreciate that proteins are likely best delivered intravenously or subcutaneously, while smaller molecules and bacterial hemophores are likely suitable for oral administration. Alternatively, a polynucleotide sequence encoding a heme binding protein could be placed in a vector and provided using gene therapy approaches. Typically, the polynucleotide sequence encoding the heme binding agent is operably linked to an expression control sequence, as is known in the art.

Kits

For use in the methods described herein, kits are also within the scope of the invention. Such kits can comprise a carrier, package or container that is compartmentalized to receive one or more containers such as vials, tubes, and the like, each of the container(s) comprising one of the separate elements (e.g., compositions, constructs) to be used in the method.

Typically, the kit comprises a composition of the invention and a vial for storage of the composition. Optionally, the kit can further comprise a syringe and/or other items for use in administration of the composition, including instructions therefore. In one embodiment, the heme-binding agent is prepared in dried form and packaged in a separate container either alone or in addition to a container of a buffer or other fluid for formation of the composition to be administered.

EXAMPLES

The following examples are presented to illustrate the present invention and to assist one of ordinary skill in making and using the same. The examples are not intended in any way to otherwise limit the scope of the invention.

Example 1

A Heme Export Protein is Required for Red Blood Cell Differentiation and Iron Homeostasis Aerobic cells require heme, a cyclic tetrapyrole containing a centrally chelated iron. It serves as the prosthetic group for hemoglobin, cytochromes, and other hemoproteins. Heme also initiates globin transcription through inhibiting the DNA binding of the repressor, Bach1(1), and globin translation through inhibiting substrate phosphorylation by the repressor, erythroid-specific eukaryotic initiation factor $2\alpha$ kinase (2). However, the trafficking of heme and its role in iron homeostasis are poorly understood.

The Feline Leukemia Virus, subgroup C (FeLV-C) receptor, FLVCR, is a heme export protein(3). Cats viremic with FeLV-C develop pure red cell aplasia (PRCA), characterized by a block in erythroid differentiation at the CFU-E (colony-forming unit-erythroid)-proerythroblast stage, reticulocytopenia, and severe anemia(4, 5). Studies with chimeric retroviruses suggest that the surface unit of the FeLV-C envelope protein induces this phenotype by blocking FLVCR function (6, 7). Although all bone marrow cells are infected(8), white cell and platelet production remain normal, which suggests that FLVCR is uniquely important for CFU-E-proerythroblast survival or differentiation.

To prove that FLVCR is required for erythropoiesis, we generated constitutive (Flvcr$^{+/-}$) and inducible (Flvcr$^{+/flox}$; Mx-cre) Flvcr mutant mice (materials and methods, FIG. S1). Interbred Flvcr$^{+/-}$ animals yielded no null offspring (Flvcr$^{-/-}$) among 109 progeny (Table S1). Intrauterine deaths occurred at one of two embryonic times: at or before embryonic day 7.5 (E7.5) and between E14.5 and E16.5.

Developmental expression of Flvcr is high in the yolk sac at E7.5, the ectoplacental cone at E8.5, and the placenta after E9.5 (FIG. 1A), all are sites of nutritional transport from mother to conceptus. These are also sites of high heme oxygenase-1 expression(9). As heme catabolism helps to support normal fetal development(9), FLVCR might complement this function at or before E7.5.

Figures 1A, 1B, 1C:
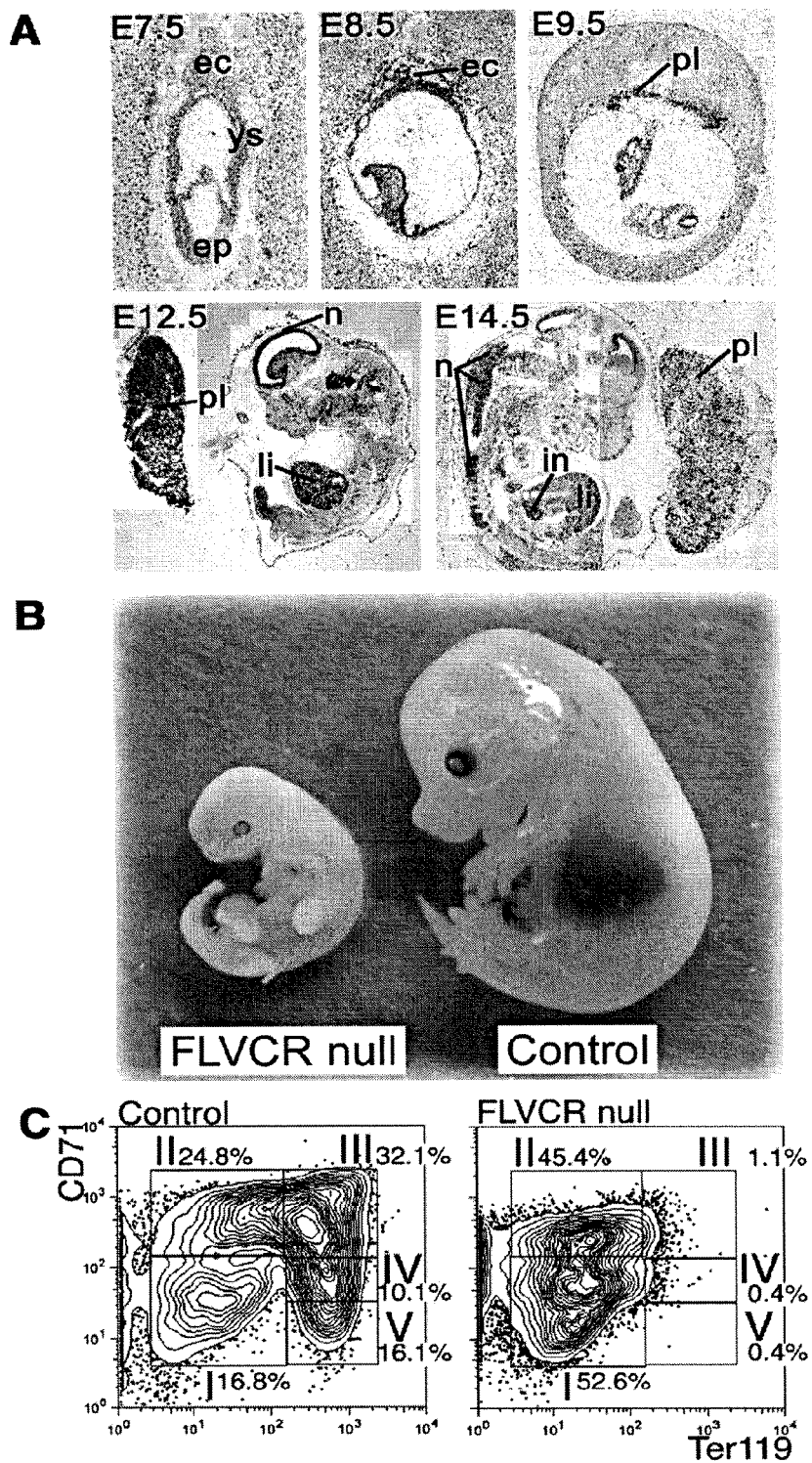
FIGS. 1A-1C. Embryonic FLVCR analyses. (1A) Wild-type mouse Flvcr expression (colored red) by in situ hybridization. Ectoplacental cone (ec), yolk sac (ys), embryo proper (ep), liver (li), neural tissue (n), placenta (pl), and intestine (in). (1B) E14.5 FLVCR-null embryo and a littermate control. The skeletal abnormalities are less apparent in embryos derived from interbreeding Flvcr$^{+/-}$-parental mice backcrossed to C57BL/6 mice for five to seven generations. (1C) Representative flow cytometric analyses of E14.5 liver cells from control and FLVCR null embryos immunostained with antibodies to CD71 and Ter119. The relative percentages of the nucleated cells in each of the populations I-V are indicated.

We hypothesize that the later death results from deficient red cell production because definitive fetal erythropoiesis in the mouse begins in the liver at ~E12(10), hepatic FLVCR expression is high from E12.5 onward (FIG. 1A), and FLVCR-null embryos have pale livers (FIG. 1B). Flow cytometric analyses of E14.5 fetal liver cells double-stained for Ter119 (erythroid-specific antigen) and CD71 (transferrin receptor) allow quantitative assessment of the maturational stages of differentiating erythroblasts(11) and confirm this concept. Normally, differentiation proceeds clockwise from population I to IV (control in FIG. 1C). In contrast, the null embryos lack Ter$_{119}^{high}$ cells, consistent with a block at the proerythroblast stage, before hemoglobinization (population II). Circulating yolk sac-derived erythroblasts do not express Flvcr by in situ hybridization and have normal morphology (FIG. S3), which indicates that embryonic (primitive) erythropoiesis does not require FLVCR.

Although the null embryos appear normal at E8.5, E10.5, and E12.5, defective growth is evident at E14.5. Mutants have abnormal limb, hand, digit maturation; flattened faces, and hypertelorism (FIG. 1B)—abnormalities that resemble human congenital PRCA, termed Diamond-Blackfan anemia (12, 13). Gross and microscopic examination of the cardiac, pulmonary, and genitourinary systems show that they are normal. Although it is theoretically possible that the observed phenotype is developmentally appropriate for a growth-retarded embryo, these specific abnormalities are not reported in other mouse models lacking definitive erythropoiesis(10, 14). Thus, FLVCR may serve roles during embryogenesis distinct from its critical erythropoietic function.

Although null animals die in utero, Flvcr$^{+/-}$ mice are clinically indistinguishable from controls (Table S2); they have low mRNA expression as anticipated, but compensate with normal FLVCR protein expression (FIG. S4).

Figure 2:
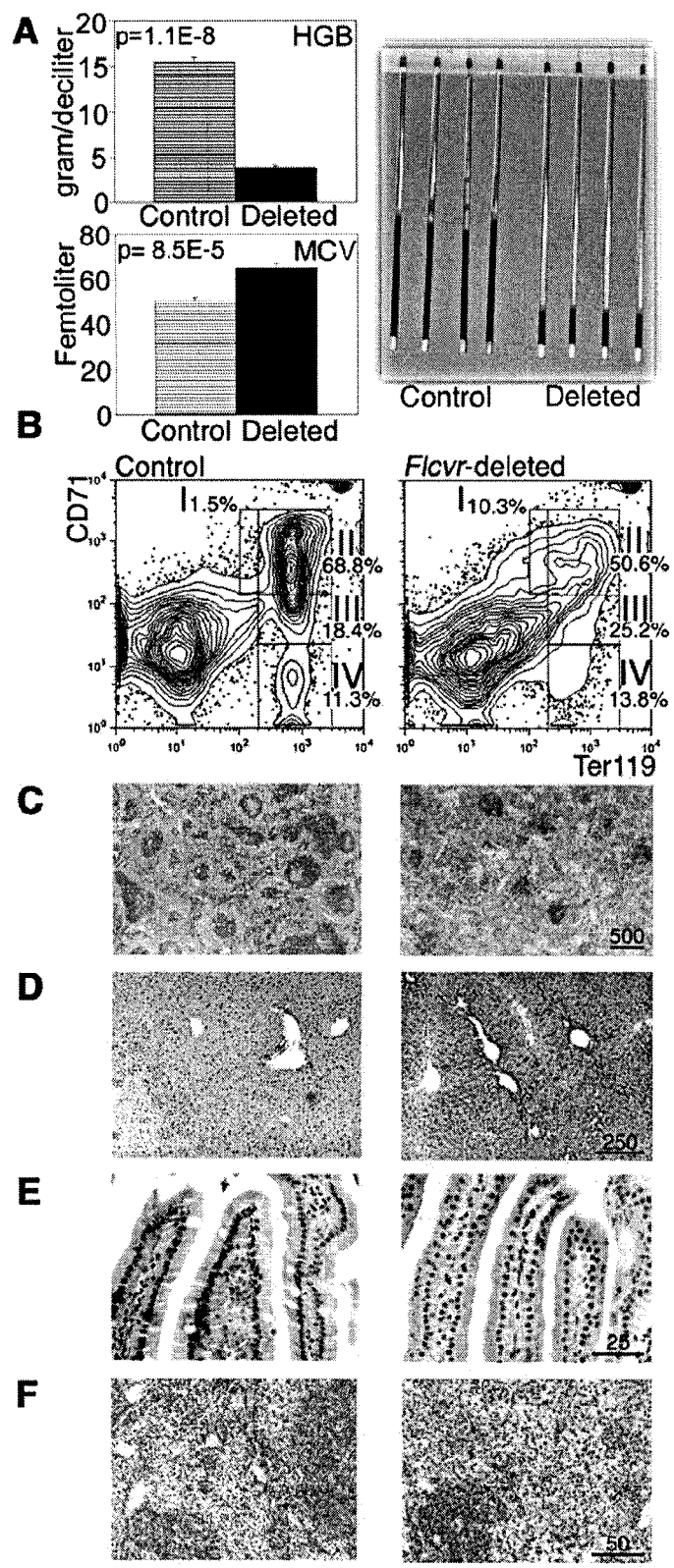
FIGS. 2A-2F. Conditional deletion of Flvcr causes PRCA. Unless noted, data are from representative 6-week-old mice, 5 weeks post deletion, (left) control (n=13), (right) Flvcr-deleted (n=11). (2A) Hematologic parameters (means±SEM, one-tailed Student's t-test), hemoglobin (HGB), mean cell corpuscular volume (MCV). Duplicate spun hematocrit tubes from two control and two Flvcr-deleted mice. (2B) Flow cytometric analyses of marrow from a control and Flvcr-deleted mouse immunostained with antibodies to CD71 and Ter119. Gating methods in FIG. 1C. Ratio of the percent of cells in population IV to I and II: deleted: Flvcr-deleted: 49.2%±11.6% (n=9) versus control: 77.1%±11.0% (n=9); means±SD, two-tailed Student's t-test, $p<10^{-4}$. The severity of block is variable between deleted animals and does not appear to correlate with the degree of anemia. (2C) Hematoxylin- and -eosin-stained spleen sections from a control and Flvcr-deleted mouse. (2D to 2F) Representative Prussian blue-stained liver sections (2D) from a 6-week-old control and a deleted mouse, and duodenum (2E) and spleen (2F) sections from an 11-week-old (10 weeks post deletion) control and a Flvcr-deleted mouse. Blue-staining indicates iron. Scale bars in microns.

We next evaluated postnatal mice lacking FLVCR [Flvcr$^{flox/flox}$; Mx-cre (FIG. S1 and FIG. 2, A to F)]. Within 4 weeks of Flvcr deletion, the mice are runted with pale paws. Necropsy reveals cardiomegaly and splenomegaly [Flvcr-deleted spleen: 326.7 mg±22.9 (n=7) vs. control spleen 72.9±5.5 (n=7); means±SEM, two-tailed Student's t-test, $p<10^{-4}$], likely responses to their severe anemia.

Peripheral blood and bone marrow findings are diagnostic of PRCA. Flvcr-deleted mice develop a severe hyperchromic macrocytic anemia (FIG. 2A and table S3) and reticulocytopenia. Flow cytometric analyses of their bone marrow, similar to liver cells from E14.5 FLVCR-null embryos, show a block in erythroid maturation at the proerythroblast stage (FIG. 2B). These results are mirrored in the spleen and account for the large spleens with expanded interfollicular regions (FIG. 2C). Erythroid colony assays confirm the flow cytometry findings; CFUs-E are absent and BFUs-E (burst-forming unit-erythroid) expand suboptimally [supporting online material (SOM) text] similar to results in cats viremic with FeLV-C(5). In addition, mice transplanted with Flvcr$^{flox/flox}$; Mx-cre bone marrow and then treated with polyinosinic-polycytidylic acid [poly(I):poly(C)] to delete Flvcr specifically in engrafted cells also develop PRCA (Table S4). This confirms that a lack of FLVCR in hematopoietic cells (and not the microenvironment) accounts for the disease.

We then evaluated the effect of FLVCR overexpression. Pep3b (CD45.1) bone marrow was transduced with retroviral vectors, MFIG or MXIG, encoding green fluorescent protein with or without human FLVCR, respectively, and transplanted into C57BL/6 (CD45.2) mouse recipients. Twelve weeks after transplantation, the MFIG mice displayed mild hypochromic, microcytic anemia. Because hypochromasia and microcytosis only result from heme or hemoglobin deficiency, FLVCR must export heme from differentiating erythroid cells in vivo. Because the anemia is mild, FLVCR does not outcompete globin for heme.

Figure 3A:
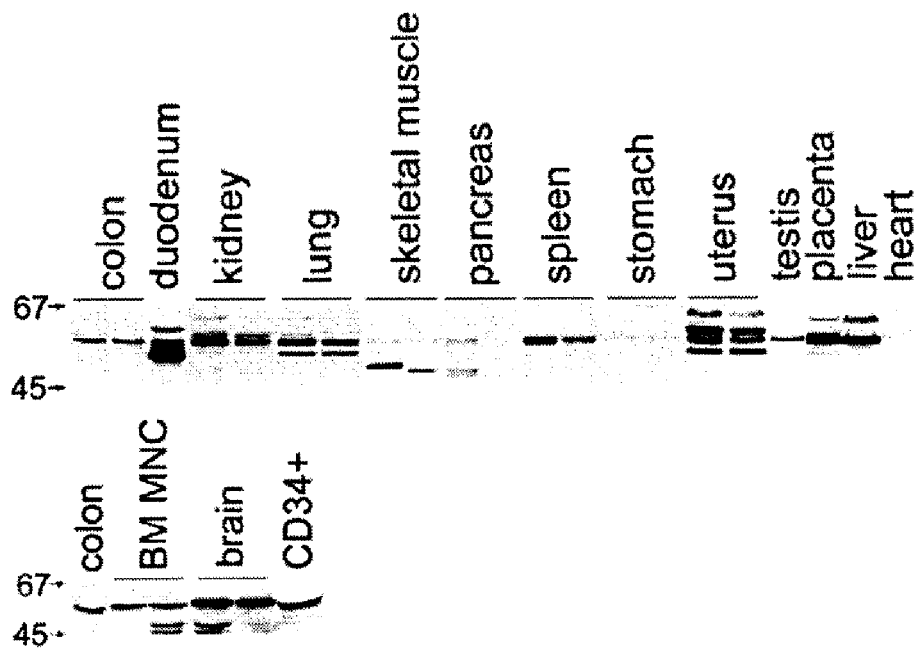
FIGS. 3A-3B. FLVCR protein levels differ in human tissues. (3A) Western blot analyses of human tissues, bone marrow mononuclear cells (BM MNC), and CD34+ stem-progenitor cells. (3B) Densities of the 60-kB FLVCR band [shown in FIG. 3A]. We also assayed FLVCR expression in macrophages isolated from human peripheral blood by plastic adherence for 2 hours, then cultured for 4 days with cytokines (intensity=5214±260). Quantitative RT-PCR confirmed that FLVCR expression is regulated post-transcriptionally (3, 23).
Figure 3B:
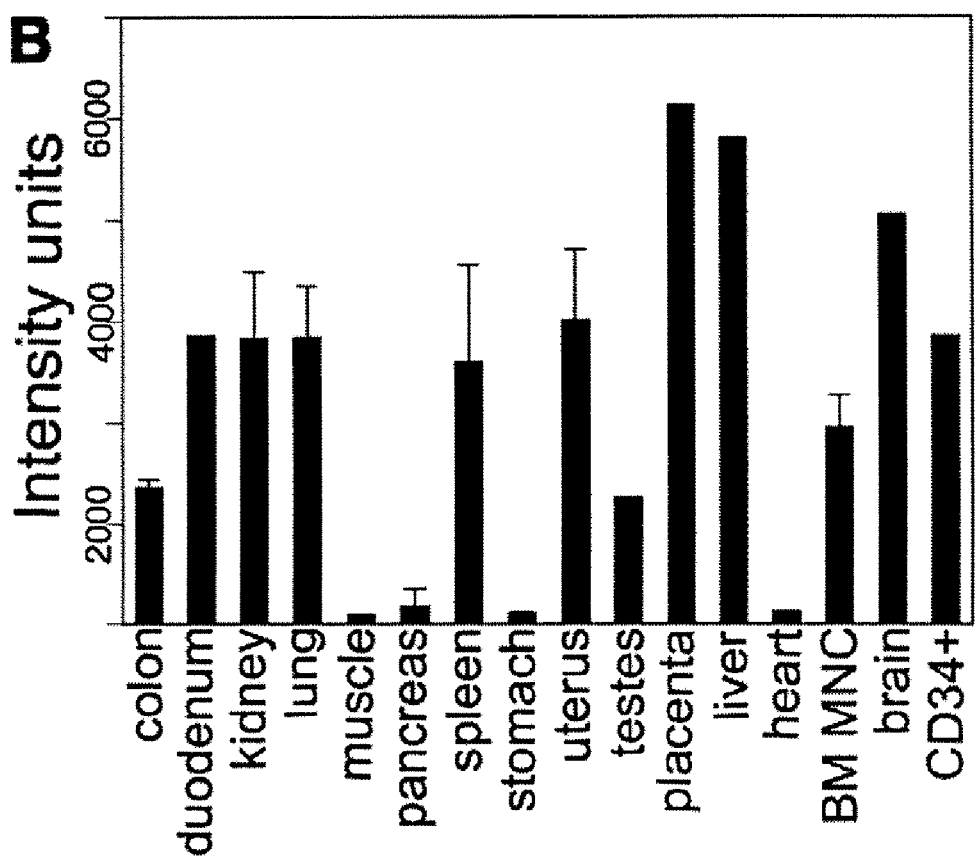

These observations lead us to hypothesize that FLVCR is required during definitive red cell differentiation to maintain intracellular free heme balance. In the absence of FLVCR, free heme, which is toxic, accumulates in proerythroblasts, the stage when heme synthesis intensifies(15), and triggers molecular pathways that result in cell apoptosis or senescence. Although this may seem counterintuitive because red cells have high heme requirements for hemoglobin, we suspect that FLVCR functions as a safety valve to protect proerythroblasts from heme toxicity when globin expression (which is transcriptionally and translationally regulated by heme, 1, 2) is insufficient. In human tissues, FLVCR is highly expressed at sites of high heme flux, including placenta, uterus, duodenum, liver, and cultured macrophages (FIG. 3), which suggests that FLVCR prevents heme toxicity or facilitates heme-iron trafficking in nonerythroid cells as well.

Figures 4A, 4B:
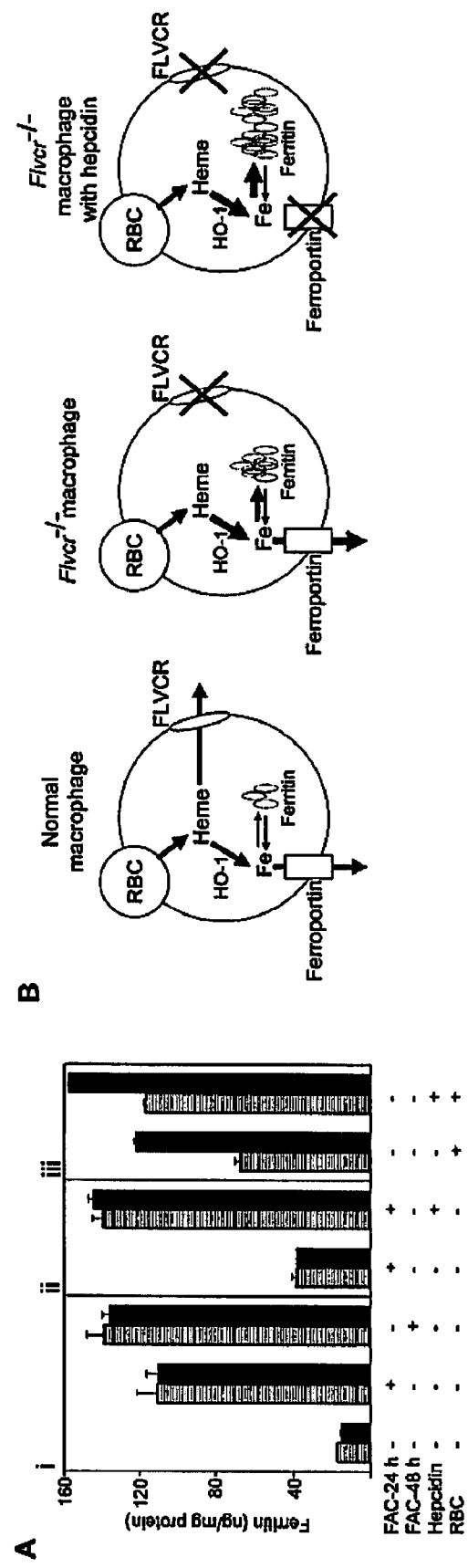
FIGS. 4A-4B. FLVCR exports heme-iron from macrophages. (4A) Bone marrow-derived macrophages from control (striped) and mice in which Flvcr was deleted neonatally (black) were incubated in the absence or presence of FAC (10 µM Fe) for 24 or 48 hours, then washed; ferritin was measured by enzyme-linked immunosorbent (ELISA) (i). Cells were incubated with FAC for 24 hours (ii) or with IgG-coated red blood cells (RBC) for 90 min (iii), washed, then incubated for an additional 24 hours with or without hepcidin (1 ug/ul) and ferritin assayed. Data represent ferritin values in macrophages derived from two control and two deleted mice±SEM of triplicate samples per mouse. (4B) Model of macrophage heme-iron recycling.
Figure 5A:
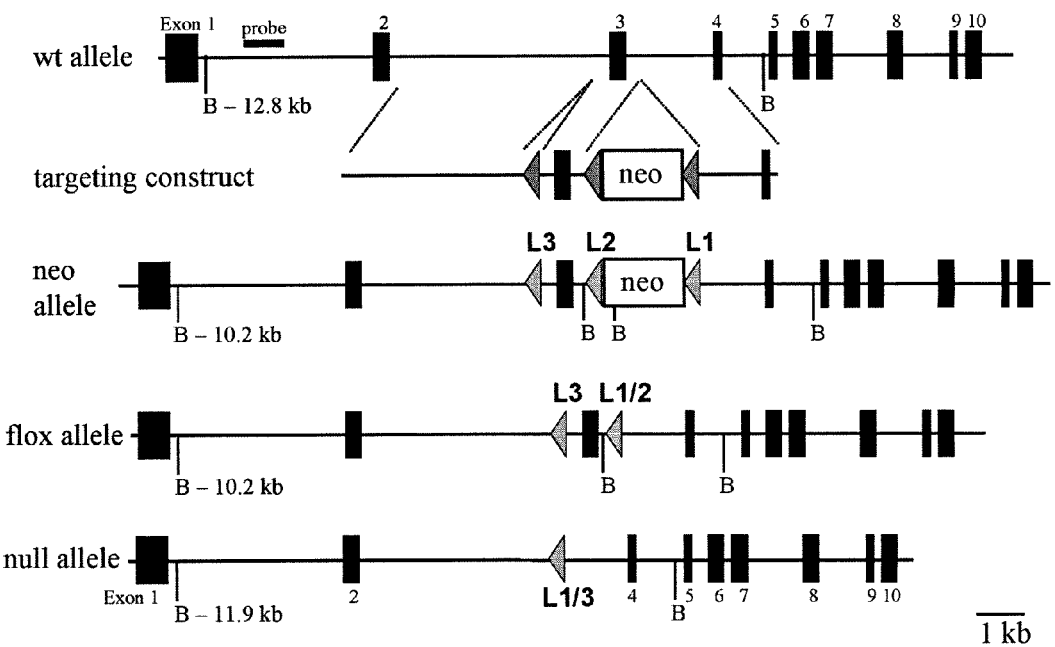
FIGS. 5A-5C. Generation of Flvcr mutant mice. 5A, Diagram of murine Flvcr genomic region and targeting strategy. The wild-type (wt) allele is depicted at the top with numbered exons. The position and size of the diagnostic BamHI (B) restriction sites and the location of the screening probe are indicated. The targeting construct shows the location of the neomycin resistance cassette and the 3 loxP sites (L1, L2, L3). The targeted allele (neo allele), flox allele, and null allele are also diagrammed with the size and position of the diagnostic restriction site indicated. 5B, Southern blot analysis of BamHI digested genomic DNA from the parental (AK7) ES line and two targeted clones (+/neo), probed with the probe indicated above. These clones were subsequently subjected to in vitro cre-mediated deletion and subclones were screened for the presence of a floxed allele (+/flox), and a null allele (+/−) by Southern blot with the same probe. 5C, PCR analysis of genomic DNA from biopsies obtained from wild-type (+/+), heterozygous floxed (+/flox), heterozygous null (+/−), or no template control samples (ntc). The primers for the L½ amplification, P1R (CAATAGACATTTAACACCCC; SEQ ID NO: 1) and P2F (CAAGAGTTCTATCTG GMCC; SEQ ID NO: 2), flank the LoxP½ element created by the cre-mediated deletion of the neomycin cassette and generate bands of 378 bp (+) and 468 bp (flox). The primers for the L3 amplification, P3R (CGGATTTTCCCAATACACAG; SEQ ID NO: 3) and P3F (AATTAAGGACTGGTGAGC GT; SEQ ID NO: 4), flank the LoxP3 element and generate bands of 569 bp (+) and 603 bp (flox). The primers for the L⅓ amplification, P1R and P3F, flank the LoxP⅓ element generated by cre-mediated deletion of exon 3 in the floxed allele and generate bands of 502 bp (−), 1369 bp (+), and 1497 bp (flox). The positions of molecular weight markers are indicated on the right.
Figure 5B:
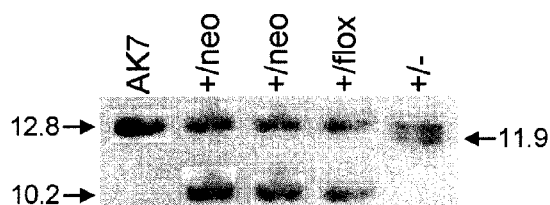
Figure 5C:
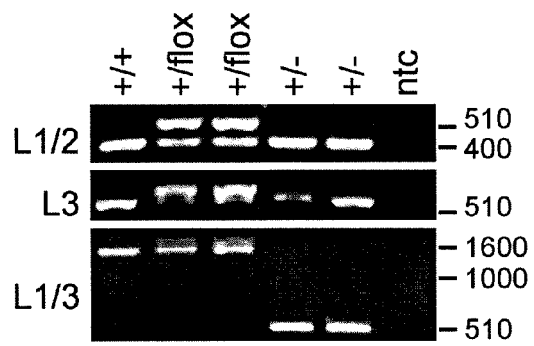
Figure 6:
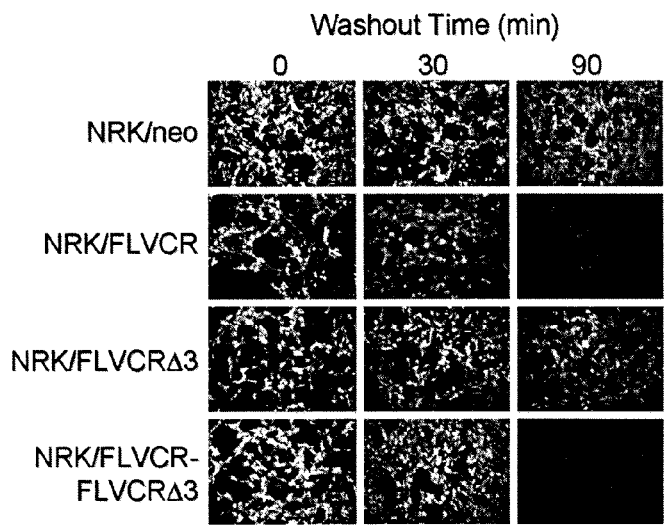
FIG. 6. Flvcr exon 3 is required for function. Cells engineered to overexpress FLVCR (NRK/FLVCR), FLVCR with exon 3 deleted (NRK/FLVCRΔ3), FLVCR and FLVCRΔ3 (NRK/FLVCR-FLVCRΔ3), and control cells (NRK/neo) were loaded with ZnMP as before (S9), then washed and incubated for 0, 30, and 90 minutes in washout buffer. When possible, panels were chosen to contain similar cell density based upon light microscopy. The analyses of ZnMP washout after 30 and 90 minutes demonstrated a reduction in NRK/FLVCR and NRK/FLVCR-FLVCRΔ3 cell fluorescence, but not in NRK/FLVCRΔ3 cell or control cell fluorescence. Cells overexpressing both wild-type and mutant FLVCR also demonstrated a reduction in cell fluorescence at 30 and 90 minutes similar to those only expressing wild-type FLVCR. This result indicates that the mutant FLVCR does not have a dominant-negative effect. Furthermore, the lack of a dominant-negative effect suggests FLVCR functions as a monomer, which is consistent with the known crystal structure of MFS members (S4, S26).
Figures 7A, 7B:
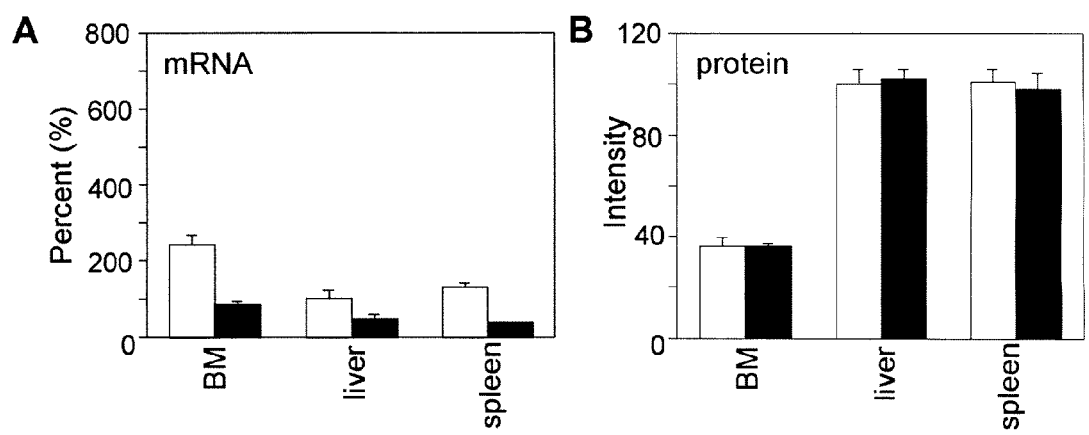
FIGS. 7A-7B. Flvcr$^{+/-}$ mice have reduced Flvcr mRNA expression but normal protein levels.

When senescent red cells are phagocytosed and digested by macrophages, hemoglobin is degraded to heme and subsequently, to iron, biliverdin, and carbon monoxide. Ferroportin exports iron to plasma transferrin for delivery to the marrow or liver(16). Hepcidin regulates this pathway by inducing the internalization and degradation of ferroportin, thereby blocking intestinal iron absorption and iron release from cellular stores and macrophages(17). To delineate the role of FLVCR in macrophage heme-iron recycling, we exposed marrow-derived macrophages from Flvcr-deleted and control mice to ferric ammonium citrate (FAC) or opsonized red blood cells in the presence or absence of hepcidin and measured ferritin (FIG. 4A). Deleted and control macrophages exposed to FAC accumulate equivalent amounts of ferritin, which increase equivalently with hepcidin treatment. However, Flvcr-deleted macrophages exposed to opsonized red cells accumulate more ferritin than controls both with and without hepcidin treatment. These data support the model of macrophage heme-iron recycling diagrammed in FIG. 4B; under normal physiologic conditions, heme can be exported via FLVCR or can be metabolized to iron, which is subsequently exported through ferroportin or stored as ferritin. When FLVCR is absent, the amount of iron that is generated exceeds ferroportin's export capacity, resulting in an increase in ferritin, which increases further if hepcidin is present and both heme-iron and inorganic iron export is blocked. Our data confirm that not all heme in macrophages is broken down(18), but rather some traverses the cell intact via FLVCR. We further verified this export function by $^{55}$Fe-heme and zinc mesoporphyrin studies (FIG. S6).

To evaluate the role of FLVCR more broadly, we examined other tissues in Flvcr-deleted mice. Within 5 weeks, mice with the deletion develop pronounced iron loading in hepatocytes and subsequently within duodenal enterocytes and splenic macrophages (FIG. 2D-F). By 7 months, there is swelling of hepatocytes lining bile canaliculi and bile stasis. In contrast, the mice in which Flvcr is deleted only in hematopoietic cells show no iron overload after 5-6 weeks (FIG. S5). Liver hepcidin expression by reverse transcription polymerase chain reaction (RT-PCR) is comparably increased in mice with the deletion [1.7±0.2 times control; deleted (n=5), control n=5; means±SEM; two-tailed Student's t-test, P=0.04] and mice lacking FLVCR only in hematopoietic cells [2.0±0.3 times control; lacking FLVCR (n=6), control (n=3), P=0.03]. These data demonstrate that hepcidin alone does not account for the iron overload and biliary pathology. One possibility consistent with our data is that FLVCR exports heme from liver into bile, thus allowing iron to exit the body.

The high hepcidin levels in Flvcr-deleted animals contrasts with levels in other iron-loading anemias with ineffective erythropoiesis, such as thalassemia and congenital dyserythropoietic anemia, where hepcidin is low despite high serum iron and systemic iron overload(19). High hepcidin levels are seen in anemic mice prevented from mounting an erythropoietic response by the use of irradiation, chemotherapy, or an antibody to erythropoietin(20, 21), which indicates that erythropoietic activity is the most potent suppressor of hepcidin synthesis. Our results demonstrate that the inhibitory signal must originate from cells more differentiated than proerythroblasts and, thus, are consistent with the recent finding that GDF15 inhibits hepcidin express ion(22).

Together, our data show that FLVCR exports heme in vivo and is required by definitive erythroid progenitors at the CFU-E-proerythroblast stage to complete terminal differentiation. We propose that heme toxicity causes PRCA in FLVCR mutant mice and FeLV-C-infected cats and may be a common pathophysiology in other models of failed erythropoiesis where heme synthesis and globin expression are dysregulated, which results in a transient excess of intracellular free heme, for example Diamond-Blackfan anemia. Our data demonstrate that FLVCR functions in macrophage heme-iron recycling and show that systemic iron balance involves heme-iron trafficking via FLVCR, in addition to the well-described elemental iron pathways.

Materials and Methods

Generation of Flvcr Mutant Mice.

Using cDNA sequences for feline and human FLVCR, we identified the cDNA sequence of murine Flvcr from EST data in the Genbank database, and confirmed this by amplification and sequencing of exons 1, 5, and 8 from genomic DNA. We next identified BAC contigs containing the entire 18 kb murine Flvcr genomic region, confirming it was the Flvcr locus and not a paralog (S1). We then derived the intron/exon structure by aligning the cDNA and genomic sequences. Due to the presence of a gene on the opposite strand that likely shares a promoter region with Flvcr (S1), we opted to delete exon 3, which encodes the intracellular loop between transmembrane domains 6 and 7, as our knockout strategy. Structure/function analyses of two proteins structurally related to FLVCR, the lactose permease and the reduced folate carrier protein, revealed that this loop is required for protein stability, processing, and function in prokaryotic and eukaryotic cells (S2-4). Exon 3 deletion should, therefore, produce an unstable protein that cannot traffic to the membrane (S2, S3). If (unexpectedly) the protein were to successfully transport to the membrane, its structure is predicted to be severely altered, making it unlikely to retain function (S5). The construct consists of a loxP site in the intron between exon 2 and exon 3, and a PGK promoter-driven neomycin selection cassette, flanked with loxP sites in the intron between exon 3 and exon 4 (FIG. S1). Primers were designed for a PCR-based cloning strategy and we generated the targeting construct using template genomic DNA that matched the strain of the ES cells (129S4/SvJae). All exons and intron-exon boundaries were sequenced in the construct and matched sequences from a BAC clone. The ES culture, transfection, cloning, and screening were performed as before (S6). Targeted clones were transfected with a cre expression vector and recloned to identify flox and null allele containing clones by Southern blot and PCR analysis. A flox containing ES clone with a normal karyotype was used for blastocyst injection and the male chimeras were bred to female C57BL/6 mice. Heterozygous Flvcr$^{+/flox}$ mice were bred to either Cmv-cre$^+$ or Mx-cre$^+$ transgenic mice (S7, S8) to generate Flvcr$^{+/-}$; Cmv-cre$^+$ or Flvcr$^{+/flox}$Mx-cre$^+$ mice, respectively. Mice were backcrossed to C57BL/6 for 1 to 5 generations then intercrossed to obtain F1, F2, and F3 generations for use in these studies.

Breeding and analysis of mutant Flvcr mice. Animals were housed in a SPF facility at the University of Washington, Seattle. The Institutional Animal Care and Use Committee approved all studies. Embryos were obtained from timed pregnant females for genotyping, immunohistochemistry, or pathologic analysis. Embryos were staged according to standard methods; noon of the day when a copulatory plug was identified is 0.5 dpc. To induce Mx-cre expression and delete exon 3, 7 day-old neonatal pups were treated with 50 μg of poly(I)-poly(C) (Amersham/GE Lifesciences, Piscataway, N.J.) IP every other day for three doses. Animals were sacrificed 5-12 weeks post deletion for analysis. Adult-deleted animals were treated with 250 μg of poly(I)-poly(C) every other day for three doses (their bone marrow was used to generate macrophages for ZnMP and $^{55}$Fe-hemin uptake and washout studies). Flvcr deletion in adults was not as effective as in neonates, however, adult animals still became severely anemic within a similar time frame.

Cell Lines

The cDNA encoding full length and mutant (lacking exon 3 coding elements) Flvcr were cloned from C57BL/6 bone marrow RNA using RT-PCR. These entire cDNAs were sequenced to confirm fidelity. These cDNA constructs were inserted into MSCVneo and MSCVhygro (Clontech Laboratories, Inc., Mountain View, Calif.) and used to generate NRK cells expressing vector alone, wild-type, mutant, or both proteins (NRK/neo, NRK/FLVCR, NRK/FLVCRΔ3 and NRK/FLVCR-FLVCRΔ3, respectively) essentially as described previously (S9).

ZnMP and $^{55}$Fe-hemin uptake and washout studies. These studies were performed as described previously (S9).

In situ hybridization. In situ hybridization of mouse embryos was performed using a 1.7 kb antisense RNA probe to murine FLVCR as described previously (S10).

Flow cytometry. Single-cell suspensions were prepared from freshly isolated bone marrow, spleen, or E14.5 fetal liver cells and were immunostained with anti-Ter119-PE and anti-CD71-FITC (BD Pharmingen, San Diego, Calif.) antibodies. Flow cytometry was performed as described previously (S11). All cells are included in the CD71-Ter119 analyses. Relative number of cells in each population I-IV as a percent of all erythroid cells is indicated. Erythroid cells are defined as all cells in populations I-IV. Single-cell suspensions of cultured macrophages were immunostained with anti-GR-1-PE (BD Pharmingen), f4/80-PE (Serotec, Raleigh, N.C.), or Mac-1-biotin followed by strepavidin-PE (BD Pharmingen).

Colony assays. Assays were performed as described previously (S12). To detect BFU-E and CFU-E colonies, $8 \times 10^5$ cells/plate were plated from Flvcr-deleted mouse marrow and $1 \times 10^5$ cells/plate from control mouse marrow in duplicate in semisolid medium (Methocult™ M3434; StemCell Technologies, Vancouver BC, Canada) according to the manufacturer's protocol.

Blood cell analysis. Mice were bled retro-orbitally into EDTA anticoagulated microtainer tubes (Becton Dickenson, Franklin Lakes, N.J.). Blood was analyzed at Phoenix Central Laboratory, Everett, Wash. on a Celidyne 3500 Analyzer or at the University of Washington on a Hemavet HV950FS analyzer (Drew Scientific, Oxford, Conn.) programmed for mouse blood. CBC (complete blood counts) include WBC (white blood cell number), RBC (red blood cell number), HGB (hemoglobin), HCT (hematocrit), MCV (mean corpuscular volume), MCH (mean cell hemoglobin), MCHC (MCH concentration), RDW (red cell distribution width), and platelet numbers.

Tissue staining. Whole mouse embryos or tissues were fixed in 10% buffered formalin, sectioned, and stained with standard hematoxylin and eosin stains or Gomori's Prussian blue stain for iron.

Murine macrophage culture. Single-cell suspensions of mouse bone marrow were collected from mice 5 days after completing poly(I)-poly(C) treatment. Cells were cultured in macrophage-differentiating media [RPMI-1640 with 30% L-cell conditioned media, 20% FBS, $10^{-4}$M β-mercaptoethanol essentially as described (S13)]. Macrophages were defined by flow cytometry (Mac-1$^+$, f4/80$^+$, GR-1$^-$) and analyzed for ZnMP and $^{55}$Fe-hemin export 10-24 days post in vivo deletion (after 5-19 days in culture).

Murine transplantation of retroviral vector-transduced bone marrow cells. GFP-expressing retroviral vectors, MXIG (Derek A. Persons, St. Jude Children's Research Hospital) (S14) and MFIG (generated by cloning the full length cDNA of human FLVCR into the cloning site upstream of the IRES of MXIG), were pseudotyped with ecotropic murine retrovirus (Phoenix Eco packaging line from Gary Nolan, Stanford, Calif.). Bone marrow was harvested from 6-12 week-old, 5-flourouracil-treated Pep3b (CD45.1) mice. Marrow cells were prestimulated with 20 ng/ml murine IL-3, 100 ng/ml human IL-6, 50 ng/ml murine stem cell factor in IMDM with 10% FBS for two days, then cultured with viral supernatant plus cytokines and 4 μg/ml of protamine sulfate on viral-preloaded RetroNectin-coated dishes (r-fibronectin CH296, Takara Bio Inc, Japan) for 6 hours. Viral supernatants were replaced by fresh media and the cells were allowed to recover overnight, and the treatment repeated. Transduced cells were transplanted into lethally irradiated C57BL/6 (CD45.2) mice ($3 \times 10^6$ cells/animal).

Transplantation Studies of Mice Lacking FLVCR in Marrow Only.

Bone marrow cells harvested from Flvcr$^{flox/flox}$; Mx-cre$^+$ mice or Mx-cre$^+$ mice were transplanted into 6-8 week-old C57/BL6 lethally irradiated (1100 CGy) female mice ($10 \times 10^6$ cells/animal). After stable engraftment (5-7 weeks), mice were treated with 250 ug poly(I)-poly(C) IP every other day for two doses and sacrificed 5.5-6 weeks later for analyses.

Quantitative RT-PCR and northern blot analyses. Q RT-PCR was performed using the TaqMan method as described (S9) for intact murine FLVCR (primers: ATCTGGAACCT-GTGCAGAAACA; SEQ ID NO: 5; and ATTGAATAAAAT-GCTCCAGTCATGAT; SEQ ID NO: 6; probe: CCCCTTTGTTCTCCTGCTGGTCAGTTATG; SEQ ID NO: 7), murine hepcidin (primers: CAGCAGAACAGAAG-GCATGATG; SEQ ID NO: 8; and GG CTGGCAAGGAG-GAGAAG; SEQ ID NO: 9; probe: CACTCGGACCCAG-GCTGCCTG SEQ ID NO: 10), and murine p-actin (primers: ACGGCCAGGTCATCACTATTG; SEQ ID NO: 11; and CAAGAAGGAAGGCTGGAAAAGA; SEQ ID NO: 12: probe: CAACGAGCGGTTCCGATGCC; SEQ ID NO: 13). To confirm hepcidin qRT-PCR results, we performed northern blot analysis as previously described (S9) using a probe directed against hepcidin (W12913.1) and normalized to β-actin expression.

Western blot analysis. Human tissues were obtained from Cooperative Human Tissues Network, Western Division at Vanderbilt University Medical Center (Nashville, Tenn.). All procedures were approved by the University of Washington Human Subjects Review Committee. Human tissues were homogenized and proteins extracted in 50 mM Tris HCL, pH 8.0, 150 mM NaCl, 1% NP-40, 0.5% DOC, and 0.1% SDS. SDS-PAGE and western blot analyses were performed as described (S9) and band intensity was quantified using Image J software, version 1.37.

Ferritin studies in macrophages. Erythrophagocytosis was performed essentially as described (S15). Alternatively, macrophages were treated with 10 μM ferric ammonium citrate (FAC). After either treatment, the cells were washed and then cultured with or without hepcidin. After 24 hrs, the samples were collected in lysis buffer (150 mM NaCl, 10 mM EDTA, 1% Triton X-100, 10 mM Tris pH 7.4), and complete protease inhibitor (Roche Diagnostics Co., Indianapolis, Ind.) and analyzed for ferritin levels as described (S16).

Supplemental Information

Additional Flvcr+/− Interbreedings: Embryonic Lethality and Morphologic Analyses.

We have now backcrossed Flvcr+/− mice to C57BL/6 mice for 5-7 generations (N5-7). Ongoing embryonic analyses of interbreedings between these mice differ from data from earlier generations of mice (presented in the main manuscript text and Table S1). Specifically, we are now finding dead, or live but morphologically identifiable, FLVCR null embryos at E12.5, when previously null and wild-type embryos were indistinguishable and alive (thus far we have distinguished 16 null embryos among 48 embryos genotyped at E12.5). Since backcrossing mice eliminates genetic variation, we are likely observing a strain-specific effect. This effect is also manifest in the morphologic analyses. Specifically, the facial and limb abnormalities present in E14.5 FLVCR null embryos are less apparent when fetal demise occurs prior to E14.5. Of note, C57BL/6 mice are characterized as a low iron-loading strain of mice compared to 129 and may not possess the genetic machinery to compensate during embryonic development when heme export is impaired. This could cause the embryos to die earlier in gestation before physical anomalies appear.

Wild-Type Mouse Embryonic Expression of Flvcr by in Situ Hybridization.

Flvcr is expressed in both the visceral endoderm and mesoderm layers of the yolk sac at E7.5 and E8.5. Mesodermal expression is generalized, consistent with expression in both blood and endothelial components. Strikingly, Flvcr is predominantly expressed in the yolk sac at E7.5 compared to the embryo proper or to the ectoplacental cone; while at E8.5, there is an increase in expression in these other tissues. During development, chorioallantoic fusion occurs at E8.5 and the embryo's source of nutrition shifts to the placenta. Thus, the extra-embryonic expression pattern of Flvcr may mirror the embryo's source of nutrition during development.

The details of Flvcr expression in the placenta are as follows: Flvcr expression is absent in the chorionic plate, but present in the labyrinth, spongiotrophoblast zone, and in the giant trophoblast cells of the placenta at E12.5 and E14.5. The outer, maternal layer of the placenta is not positive. Some but not all of the giant trophoblast cells at E8.5 express Flvcr mRNA.

Colony Assay Results in Flvcr-Deleted Animals and Controls.

CFU-E colonies are absent in marrow from Flvcr-deleted animals (deleted: 0.0 colonies/$10^5$ cells plated±0, n=4 vs. control: 169.7±57.8, n=3; mean±SD, two-tailed Student's t-test, p=0.04). The number of BFU-E colonies in deleted mice, defined both by morphology and a criteria of a minimum of 200 cells per colony, is 12.0±6.5 colonies/$10^5$ cells plated (n=4) verses 53.8±29.7 in control mice (n=4; mean±SD, two-tailed Student's t-test, p=0.06). CFU-GM colonies are smaller than control colonies (1-15 cells/colony vs. >30 cells/colony). These data are consistent with a block in erythroid differentiation at the CFU-E/proerythroblast stage since the colonies counted on day 7 in a BFU-E assay contain erythroid cells that derive from BFU-E present at the time of plating. The assay thus requires that BFU-E differentiate to CFU-E and proerythroblasts and begin hemoglobinization to be enumerated; likewise, the colonies counted on day 2 in a CFU-E assay are a representation of a CFU-E present at the time of plating, and thus require that cells proceed through the proerythroblast stage for inclusion in the CFU-E colony count. Therefore, we expect to see poorly formed BFU-E colonies or fewer BFU-E colony number (since they would not meet the criteria of ≧900 cells/colony) and no CFU-E colonies when differentiation fails at the CFU-E/proerythroblast stage. We hypothesize that the abnormal CFU-GM colony morphology in Flvcr-deleted mice is due to dysfunctional monocytes and macrophages which lack FLVCR.

Overexpression of FLVCR Results in a Mild Microcytic Anemia.

Pep3b bone marrow (CD45.1+) was transduced with retroviral vectors, MFIG and MXIG, encoding GFP with or without human FLVCR. Transduction efficiency measured by GFP was 93.1% for MFIG and 94.1% for MXIG transduced cells. Transduced marrow was then transplanted into irradiated C57BL/6 recipients (CD45.2+). Peripheral blood and marrow mononuclear cells were collected 12 weeks after transplantation. All mice included in this analysis demonstrated excellent engraftment (percent of granulocytes expressing donor CD45.1: MFIG: 95.9±3.0, n=3, and MXIG: 86.9%±7.0, n=3; mean±SD, two-tailed Student's t-test, p=0.14). 56.8±34.7 and 59.2%±28.3 of granulocytes (p=0.93) expressed GFP in the MFIG and MXIG mice, respectively. Twelve weeks after transplantation, the MFIG mice have a mild hypochromic, microcytic anemia (MFIG: MCH 12.7 pg±1.7, HGB 13.2 g/dl±1.4, MCV 41.0 fL±5.2, n=3 vs. MXIG: MCH 15.7±1.7, HGB 15.4±0.5, MCV 49.3±1.2; mean±SD, n=3, one-tailed Student's t-test, p=0.05, 0.05, and 0.05 respectively).

Heme Toxicity and Erythropoiesis Failure: Possible Link to Diamond-Blackfan Anemia.

Diamond-Blackfan anemia (DBA) is a congenital form of PRCA in humans characterized by a macrocytic anemia, reticulocytopenia, and a block in erythroid differentiation at the proerythroblast stage (S17) like FeLV-C-associated PRCA and PRCA in Flvcr-deleted mice. Heterozygous mutations in RPS19, which encodes a protein that binds to the 40S (translation initiation) ribosomal subunit as one of 33 associated proteins, account for 25% of DBA cases (S18). Recently, mutations in two other ribosomal proteins, RPS24 and RPS17, which also bind to the 40S subunit, have been identified in a subset of DBA patients (S19, S20). RPS19 mutations result in defective maturation of the 40S ribosomal subunit (S21). These mutations should, therefore, result in a slow or late initiation of globin translation, and consequently, to transient excess in intracellular free heme, analogous to what we predict occurs in the Flvcr-deleted (or FLVCR null) mice where heme export is impaired.

While we anticipated that Flvcr-deleted mice and DBA patients would share a common erythroid phenotype, we were surprised to discover that E14.5 FLVCR null embryos exhibit the same, unique morphologic abnormalities seen in DBA, specifically, flattened faces, hypertelorism (S22), upper limb, and hand/digit abnormalities (S23-25). This convergent phenotype raises the possibility that FLVCR, heme excess, or related pathways account for both the congenital deformities and the erythroid defect in DBA patients.

FLVCR mRNA Expression in Multiple Human Tissues by Quantitative RT-PCR.

We confirmed that FLVCR mRNA expression does not equate to FLVCR protein levels by performing quantitative RT-PCR on the same tissue samples analyzed by western blot analysis (FIG. S3A-B). mRNA levels were comparable in all tissue samples. Specifically, mRNA copy number ranged from 1590 copies (per 50 ng RNA) in the pancreas, to 2164 in the stomach, and to 2607 in the duodenum. The discrepancy between mRNA and protein expression implies that FLVCR is regulated at the protein level.

TABLE S1

Genotyping of mutant Flvcr embryos and pups derived from F1, F2, or F3 intercrosses. The number of mice and percentage (%) with each genotype are indicated. The observed ratios of the genotypes are presented relative to wild-type. Chi-square value = 27.25, one degree of freedom, p < 0.001. In subsequent embryonic analyses from interbreedings between Flvcr$^{+/-}$ parental mice, which were backcrossed to C57BL/6 mice for 5-7 generations (resulting in a purer C57BL/6 background), the late stage embryonic death occurred at or before E12.5.

| Age | Genotype | | | Ratio |
|---|---|---|---|---|
| | +/+ | +/- | -/- | |
| E7.5 | 12 (27.9) | 24 (55.8) | 7 (16.2) | 1:2:0.6 |
| E8.5 | 9 (31) | 17 (58.6) | 3 (10.3) | 1:1.9:0.3 |
| E10.5 | 4 (22.2) | 11 (61.1) | 3 (16.7) | 1:2.8:0.8 |
| E12.5 | 5 (27.8) | 12 (66.7) | 1 (5.5) | 1:2.4:0.2 |
| E14.5 | 13 (29.5) | 25 (56.8) | 6 (13.6) | 1:1.9:0.5 |
| E16.5 | 6 (33.3) | 12 (66.7) | 0 (0) | 1:2:0 |
| 4 wks | 34 (31.1) | 75 (68.8) | 0 (0) | 1:2.2:0 |
| Summary: | | | | |
| E7.5-E14.5 | 43 (28.3) | 89 (58.6) | 20 (13.2) | 1:2.1:0.5 |
| After E14.5 | 40 (31.5) | 87 (68.5) | 0 (0) | 1:2.2:0 |

TABLE S2

Flvcr$^{+/-}$ mice hematologic parameters. Control mice n = 8, Flvcr$^{+/-}$ mice n = 7; mean ± SEM, two-tailed Student's t-test.

| CBC parameter | Control | Flvcr$^{+/-}$ | p value |
|---|---|---|---|
| WBC (k/µl) | 7.9 ± 0.9 | 9.7 ± 0.6 | 0.13 |
| RBC (M/µl) | 9.7 ± 0.3 | 9.5 ± 0.1 | 0.47 |
| HGB (g/dl) | 14.8 ± 0.5 | 14.3 ± 0.1 | 0.32 |
| HCT (%) | 42.1 ± 1.3 | 40.7 ± 0.4 | 0.34 |
| MCV (fL) | 43.3 ± 0.2 | 42.9 ± 0.3 | 0.24 |
| MCH (pg) | 15.2 ± 0.1 | 15.0 ± 0.2 | 0.35 |
| MCHC (%) | 35.2 ± 0.2 | 35.1 ± 0.2 | 0.76 |
| RDW (%) | 17.9 ± 0.2 | 17.5 ± 0.1 | 0.10 |
| platelets (k/µl) | 1095 ± 61 | 116 ± 54 | 0.80 |

TABLE S3

Flvcr-deleted mice hematologic parameters. Control mice n = 13, Flvcr-deleted mice n = 11; mean ± SEM, one-tailed Student's t-test. The absolute neutrophil and lymphocyte counts of deleted and control animals did not significantly differ.

| CBC parameter | Control | Deleted | p value |
|---|---|---|---|
| WBC (k/µl) | 7.8 ± 0.9 | 4.7 ± 0.8 | 0.007 |
| RBC (M/µl) | 9.8 ± 0.3 | 3.0 ± 0.5 | $1.9 \times 10^{-8}$ |
| HGB (g/dl) | 15.4 ± 0.5 | 3.8 ± 0.2 | $1.1 \times 10^{-12}$ |
| HCT (%) | 49.6 ± 2.0 | 13.2 ± 1.1 | $1.5 \times 10^{-12}$ |
| MCV (fL) | 50.8 ± 1.5 | 65.5 ± 2.1 | $8.5 \times 10^{-5}$ |
| MCH (pg) | 15.9 ± 0.5 | 22.7 ± 0.6 | $7.7 \times 10^{-7}$ |
| MCHC (%) | 31.2 ± 0.4 | 34.8 ± 1.2 | 0.013 |
| RDW (%) | 18.3 ± 0.9 | 28.9 ± 1.7 | $3.9 \times 10^{-4}$ |
| platelets (k/µl) | 1104 ± 140 | 3626 ± 252 | $1.9 \times 10^{-7}$ |

TABLE S4

Hematologic parameters of mice lacking FLVCR only in the bone marrow. Control mice n = 3, mice transplanted with Flvcr$^{flox/flox}$; Mx-cre$^+$ marrow and then treated with poly(I)-poly(C) to delete Flvcr in hematopoietic cells n = 6; mean ± SEM, one-tailed Student's t-test. Data obtained 5.5-6 weeks post poly(I)-poly(C) treatment. White blood cell analyses excluded as the mice received sedation prior to blood draw which dramatically altered WBC parameters. CD71/Ter119 flow cytometric analyses of bone marrow and spleen from mice lacking FLVCR only in the marrow were comparable to analyses of neonatally-deleted Flvcr mice; similarly, CFU-E colonies were absent in mice lacking FLVCR only in the marrow.

| CBC parameter | Control | without FLVCR | p value |
|---|---|---|---|
| RBC (M/µl) | 9.4 ± 0.7 | 3.64 ± 0.3 | $3.7 \times 10^{-3}$ |
| HGB (g/dl) | 13.0 ± 0.2 | 5.53 ± 0.5 | $1.8 \times 10^{-6}$ |
| HCT (%) | 41.6 ± 3.0 | 17.6 ± 2.2 | $1.3 \times 10^{-3}$ |
| MCV (fL) | 44.3 ± 0.3 | 47.5 ± 2.7 | 0.15 |
| MCH (pg) | 13.9 ± 0.7 | 15.2 ± 0.6 | 0.12 |
| MCHC (%) | 31.4 ± 1.7 | 32.3 ± 1.6 | 0.35 |
| RDW (%) | 18.6 ± 0.5 | 29.7 ± 4.2 | 0.02 |
| platelets (k/µl) | 761.7 ± 92.9 | 1921.2 ± 374.8 | 0.01 |

References Cited in Example 1

1. T. Tahara et al., *J. Biol. Chem.* 279, 5480 (2004).
2. M. Rafie-Kolpin et al., *J. Biol. Chem.* 275, 5171 (2000).
3. J. G. Quigley et al., *Cell* 118, 757 (2004).
4. N. G. Testa, et al., *Leuk. Res.* 7, 103 (1983).
5. J. L. Abkowitz, *Blood* 77, 1442 (1991).
6. N. Riedel, et al., *Proc. Natl. Acad. Sci. USA* 85, 2758 (1988).
7. M. A. Rigby et al., *J. Gen. Virol.* 73, 2839 (1992).
8. J. L. Abkowitz, R. D. Holly, C. K Grant, *J. Clin. Invest.* 80, 1056 (1987).
9. S. Watanabe, et al., *Placenta* 25, 387 (2004).
10. H. Wu, X. Liu, R. Jaenisch, H. F. Lodish, *Cell* 83, 59 (1995).
11. J. Zhang, M. Socolovsky, A. W. Gross, H. F. Lodish, *Blood* 102, 3938 (2003).
12. I. A. Cathie, *Arch Dis Child* 25, 313 (1950).
13. T. N. Willig et al., *Pediatr. Res.* 46, 553 (1999).
14. V. E. Wang, et al., *Mol. Cell. Biol.* 24, 1022 (2004).
15. A. Wickrema, et al., *Blood* 80, 1940(1992).
16. M. W. Hentze, M. U. Muckenthaler, N. C. Andrews, *Cell* 117, 285 (2004).
17. E. Nemeth et al., *Science* 306, 2090 (2004).
18. M. D. Knutson, et al., *Proc. Natl. Acad. Sci. USA* 102, 1324 (2005).
19. G. Papanikolaou et al., *Blood* 105, 4103 (2005).
20. M. Vokurka, J. Krijt, K. Sulc, E. Necas, *Physiol Res* 55, 667 (2006).
21. M. Pak, et al., *Blood* 108, 3730 (2006).
22. T. Tanno et al., *Nat. Med.* 13, 1096 (2007).
23. C. S. Tailor, B. J. Willett, D. Kabat, *J. Virol.* 73, 6500 (1999).
S1. L. Lipovich, et al., *Gene* 286, 203 (2002).
S2. A. B. Weinglass, H. R. Kaback, *Proc. Natl. Acad. Sci. USA* 97, 8938 (2000).
S3. H. Sadlish, F. M. Williams, W. F. Flintoff, *Biochem. J.* 364, 777 (2002).
S4. T. Hirai et al., *Nat. Struct. Biol.* 9, 597 (2002).
S5. G. E. Tusnady, I. Simon, *J. Mol. Biol.* 283, 489 (1998).
S6. R. T. Doty, et al., *Blood Cells Mol. Dis.* 28, 407 (2002).
S7. M. Lakso et al., *Proc. Natl. Acad. Sci. USA* 89, 6232 (1992).
S8. R. Kuhn, F. Schwenk, M. Aguet, K. Rajewsky, *Science* 269, 1427 (1995).

S9. J. G. Quigley et al., *Cell* 118, 757 (2004).
S10. P. D. Kingsley et al., *Blood* 107, 1665 (2006).
S11. M. Socolovsky et al., *Blood* 98, 3261 (2001).
S12. D. W. Kennedy, J. L. Abkowitz, *Blood* 90, 986 (1997).
S13. J. A. Swanson, *J. Cell Sci* 94 (Pt 1), 135 (1989).
S14. D. A. Persons et al., *Blood* 93, 488 (1999).
S15. M. D. Knutson, et al., *Blood* 102, 4191 (2003).
S16. E. Nemeth et al., *Science* 306, 2090 (2004).
S17. Y. Ohene-Abuakwa, K. A. Orfali, C. Marius, S. E. Ball, *Blood* 105, 838 (2005).
S18. N. Draptchinskaia et al., *Nat. Genet.* 21, 169 (1999).
S19. H. T. Gazda et al., *Am. J Hum. Genet.* 79, 1110 (2006).
S20. R. Cmejla, et al., *Hum Mutat* 28, 1178(2007).
S21. J. Flygare et al., *Blood* 109, 980 (2007).
S22. I. A. Cathie, *Arch Dis Child* 25, 313 (1950).
S23. S. E. Ball, et al., *Br. J. Haematol.* 94, 645 (1996).
S24. T. N. Willig et al., *Pediatr. Res.* 46, 553 (1999).
S25. A. Vlachos, et al., *J. Pediatr. Hematol. Oncol.* 23, 377 (2001).
S26. J. Abramson et al., *Science* 301, 610 (2003).

Example 2

Evidence that Heme Export Via the Feline Leukemia Virus, Subgroup, C Receptor (FLVCR) is Carrier Dependent and its Physiological Implications FLVCR is a heme export protein that is required for pro-erythroblast survival (1), macrophage heme-iron recycling, and systemic iron homeostasis (2). However, the mechanism and regulation of export through this and related major facilitator superfamily (MFS) members (e.g. OxIT, LacY, GlpT) is unknown. To gain insights into the structure and function of FLVCR, we first studied the export of zinc mesoporphyrin (ZnMP), a fluorescent heme analog that traffics similarly to heme and also blocks heme oxygenase activity. NRK (rat) cells engineered to express human FLVCR were loaded with ZnMP for 30 min, then incubated at 37° C. for 90 min with no carrier protein, albumin, or hemopexin (Hpx). In the absence of carrier protein, no export was seen. Export was near complete in the presence of 151.5 µM (1%) albumin, but less extensive with 15.15 µM albumin and almost absent with 1.151 µM albumin. Interestingly, Hpx appeared 100 fold more efficacious in inducing ZnMP export. Comparable results were obtained in studies of human blood macrophages using either ZnMP or $^{55}$Fe-heme. As Kds are ~10 nM and <1 pM, for albumin and Hpx, respectively, our data argue that the rate and efficiency of heme export depends on the avidity of heme binding. Interestingly, there are three conserved histidine residues in FLVCR, two of which (aa 145 and 198) are 52 residues apart on adjacent ($1^{st}$ and $2^{nd}$) extracellular loops. Based upon known MFS member structures (3), these histidines are optimally located to coordinate the heme-iron exiting the channel while the adjacent transmembrane regions contain several aromatic residues capable of lining a solvent accessible heme pocket. These histidine residues are conserved in human, cat, and mouse FLVCR, but are not present in closely related paralogs (4), which lack heme export function. We hypothesize that they act as a temporary docking site for heme after it exits through a transport channel and prior to being picked up by Hpx in the circulation, and thus as a structural regulator of export efficiency, or have another physiological function. We are currently using site-directed mutagenesis to generate mutant FLVCR and will test export function in transduced NRK cells and in vivo in mice. Since Hpx is present in a high concentration in human serum (1 mg/ml, 16.67 µM, equivalent to transferrin (1.8-2.5 mg/ml, 22-31 µM)), it may function physiologically to facilitate the recycling of heme-iron from macrophages after they ingest senescent red cells, in addition to its role as a scavenger protein for protection from internal bleeding or extravascular hemolysis.

FLVCR is highly expressed in liver, duodenum, and spleen, which are sites of iron transit. Our studies of polarized HepG2 (liver) cells show that FLVCR co-localizes with villin at the apical surface, which is the bile canalicular surface. FLVCR traffics to the apical surface of both hepatic and duodenal cells in vitro when the intracellular iron levels are high. These data, coupled with the finding of liver iron overload in FLVCR-deleted mice (2), suggest that FLVCR may export heme from liver into bile, thus allowing iron to exit the body. It is possible, that chelating heme, not only iron, might ameliorate the anemia of chronic inflammation or the systemic iron overload of hemochromatosis or other disorders.

References Cited in Example 2

1. Cell 118: 757-766, 2004
2. Example 1, above, also published in Science 319:825-828, 2008
3. Protein Science 13:1832-1840, 2004
4. Gene 286:203-213, 2002

Those skilled in the art will appreciate that the conceptions and specific embodiments disclosed in this description may be readily utilized as a basis for modifying or designing other embodiments for carrying out the same purposes of the present invention. Those skilled in the art will also appreciate that such equivalent embodiments do not depart from the spirit and scope of the invention as set forth in the appended claims.

Throughout this application various publications are referenced. The disclosures of these publications in their entireties are hereby incorporated by reference into this application in order to describe more fully the state of the art to which this invention pertains.

What is claimed is:

1. A method of facilitating heme-iron export from a cell comprising contacting the cell with a heme-binding agent, wherein the heme-binding agent is hemopexin, a synthetic heme binder, a bacterial hemophore or a bacterial heme-binding protein, and wherein the heme-iron is exported from the cell.

2. The method of claim 1, wherein the cell is a developing red blood cell.

3. The method of claim 1, wherein the heme-binding agent is hemopexin.

4. The method of claim 1, wherein the heme-binding agent is selected from the group consisting of: heme-binding protein 23 (HBP23); adrenal inner zone antigen (IZA1); rhodnius heme-binding protein (RHBP); NADPH-dependent methemoglobin reductase; histidine-rich protein 2 (HRP-2); damage resistance protein 1 (Dap1p); HupA, HpbA, ShuT, PhuS and HemS.

5. The method of claim 1, wherein the heme-binding agent comprises a heme-binding site having two histidines that are 43-52 amino acids apart and hydrophobic amino acids lining a heme binding pocket.

6. The method of claim 1, wherein the heme-binding agent has binds heme with a Kd of up to 1 nM.

7. The method of claim 1, wherein the bacterial heme-binding protein comprises *S. dysenteriae* heme shuttle protein ShuT.

8. A method of treating a disorder associated with excess iron in cells in a subject comprising administering to the subject an effective amount of a heme-binding agent, wherein the heme-binding agent is hemopexin, a synthetic heme binder, a bacterial hemophore or a bacterial heme-binding protein, and wherein the disorder is treated.

9. The method of claim 8, wherein the disorder is anemia.

10. The method of claim 9, wherein the anemia is associated with inflammation, myelodysplasia or ineffective erythropoiesis.

11. The method of claim 8, wherein the disorder is an iron overload disorder.

12. The method of claim 11, wherein the disorder is hemochromatosis.

13. The method of claim 8, wherein the administering is intravenous or subcutaneous.

14. The method of claim 8, wherein the administering is oral.

15. The method of claim 8, wherein the heme-binding agent is hemopexin.

16. The method of claim 8, wherein the heme-binding agent is selected from the group consisting of: heme-binding protein 23 (HBP23); adrenal inner zone antigen (IZA1); rhodnius heme-binding protein (RHBP); NADPH-dependent methemoglobin reductase; histidine-rich protein 2 (HRP-2); damage resistance protein 1 (Dap1p); HupA, HpbA, ShuT, PhuS and HemS.

17. The method of claim 8, wherein the heme-binding agent comprises a heme-binding site having two histidines that are 43-52 amino acids apart and hydrophobic amino acids lining a heme binding pocket.

18. The method of claim 8, wherein the heme-binding agent binds heme with a Kd of up to 1 nM.

19. The method of claim 8, wherein the heme-binding agent binds heme with a Kd of up to 1 μM.

20. The method of claim 8, wherein the heme-binding agent is provided in polypeptide form.

* * * * *

UNITED STATES PATENT AND TRADEMARK OFFICE
CERTIFICATE OF CORRECTION

| | | |
|---|---|---|
| PATENT NO. | : 8,119,773 B2 | Page 1 of 1 |
| APPLICATION NO. | : 12/329206 | |
| DATED | : February 21, 2012 | |
| INVENTOR(S) | : Abkowitz et al. | |

It is certified that error appears in the above-identified patent and that said Letters Patent is hereby corrected as shown below:

At Column 25, Claim 6, line 2, delete "has"

At Column 26, Claim 19, line 17, "1 µM" should read --1 pM--

Signed and Sealed this
Twenty-ninth Day of May, 2012

David J. Kappos
*Director of the United States Patent and Trademark Office*

SEQUENCE LISTING

```
<160> NUMBER OF SEQ ID NOS: 13

<210> SEQ ID NO 1
<211> LENGTH: 20
<212> TYPE: DNA
<213> ORGANISM: artificial sequence
<220> FEATURE:
<223> OTHER INFORMATION: primer

<400> SEQUENCE: 1
```
caatagacat ttaacacccc          20

<210> SEQ ID NO 2
<211> LENGTH: 20
<212> TYPE: DNA
<213> ORGANISM: artificial sequence
<220> FEATURE:
<223> OTHER INFORMATION: primer

<400> SEQUENCE: 2
caagagttct atctggaacc          20

<210> SEQ ID NO 3
<211> LENGTH: 20
<212> TYPE: DNA
<213> ORGANISM: artificial sequence
<220> FEATURE:
<223> OTHER INFORMATION: primer

<400> SEQUENCE: 3
cggattttcc caatacacag          20

<210> SEQ ID NO 4
<211> LENGTH: 20
<212> TYPE: DNA
<213> ORGANISM: artificial sequence
<220> FEATURE:
<223> OTHER INFORMATION: primer

<400> SEQUENCE: 4
aattaaggac tggtgagcgt          20

<210> SEQ ID NO 5
<211> LENGTH: 22
<212> TYPE: DNA
<213> ORGANISM: artificial sequence
<220> FEATURE:
<223> OTHER INFORMATION: primer

<400> SEQUENCE: 5
atctggaacc tgtgcagaaa ca       22

<210> SEQ ID NO 6
<211> LENGTH: 26
<212> TYPE: DNA
<213> ORGANISM: artificial sequence
<220> FEATURE:
<223> OTHER INFORMATION: primer

<400> SEQUENCE: 6
attgaataaa atgctccagt catgat   26

<210> SEQ ID NO 7
<211> LENGTH: 29
<212> TYPE: DNA
<213> ORGANISM: artificial sequence
<220> FEATURE:
<223> OTHER INFORMATION: probe

<400> SEQUENCE: 7
cccctttgtt ctcctgctgg tcagttatg    29

<210> SEQ ID NO 8
<211> LENGTH: 22
<212> TYPE: DNA
<213> ORGANISM: artificial sequence
<220> FEATURE:

```
<223> OTHER INFORMATION: primer

<400> SEQUENCE: 8
cagcagaaca gaaggcatga tg                                              22

<210> SEQ ID NO 9
<211> LENGTH: 19
<212> TYPE: DNA
<213> ORGANISM: artificial sequence
<220> FEATURE:
<223> OTHER INFORMATION: primer

<400> SEQUENCE: 9
ggctggcaag gaggagaag                                                  19

<210> SEQ ID NO 10
<211> LENGTH: 21
<212> TYPE: DNA
<213> ORGANISM: artificial sequence
<220> FEATURE:
<223> OTHER INFORMATION: probe

<400> SEQUENCE: 10
cactcggacc caggctgcct g                                               21

<210> SEQ ID NO 11
<211> LENGTH: 21
<212> TYPE: DNA
<213> ORGANISM: artificial sequence
<220> FEATURE:
<223> OTHER INFORMATION: primer

<400> SEQUENCE: 11
acggccaggt catcactatt g                                               21

<210> SEQ ID NO 12
<211> LENGTH: 22
<212> TYPE: DNA
<213> ORGANISM: artificial sequence
<220> FEATURE:
<223> OTHER INFORMATION: primer

<400> SEQUENCE: 12
caagaaggaa ggctggaaaa ga                                              22

<210> SEQ ID NO 13
<211> LENGTH: 21
<212> TYPE: DNA
<213> ORGANISM: artificial sequence
<220> FEATURE:
<223> OTHER INFORMATION: probe

<400> SEQUENCE: 13
caacgagcgg ttccgatgcc c                                               21
```